United States Patent
Herold

(10) Patent No.: US 6,635,783 B2
(45) Date of Patent: Oct. 21, 2003

(54) BICYCLIC 1,3-AMINOALCOHOLS, D8-METAL COMPLEXES AND HYDROGENATION PROCESSES

(75) Inventor: Peter Herold, Basel (CH)

(73) Assignee: Solvias AG, Basel (CH)

(*) Notice: Subject to any disclaimer, the term of this patent is extended or adjusted under 35 U.S.C. 154(b) by 79 days.

(21) Appl. No.: 09/798,957

(22) Filed: Mar. 6, 2001

(65) Prior Publication Data

US 2002/0010085 A1 Jan. 24, 2002

(30) Foreign Application Priority Data

Mar. 6, 2000 (CH) .............................................. 434/00

(51) Int. Cl.[7] ..................... C07C 211/35; C07C 233/23; C07C 275/26; C07C 311/07; C07F 9/36
(52) U.S. Cl. .......................... 560/115; 564/12; 564/57; 564/80; 564/90; 564/95; 564/222; 564/307; 564/414; 564/460
(58) Field of Search ............................ 560/115; 564/12, 564/57, 80, 90, 95, 222, 217, 307, 460, 414; 548/221; 502/166, 167

(56) References Cited

U.S. PATENT DOCUMENTS 4,837,218 A * 6/1989 Olney .......................... 514/646
5,583,221 A * 12/1996 Hu et al. ..................... 540/520

FOREIGN PATENT DOCUMENTS

| CA | 2239970 | 6/1997 |
| WO | 98-42643 | 10/1998 |

OTHER PUBLICATIONS

Hutchinson, Sally A.; Baker, Stephen P.; Scammells, Peter J., Bioorg. Med. Chem. Lett., 9(7), 933–936 (English) 1999.*
Edwards, Oliver E.; Elder, John W.; Lesage, Maurice; Retallack, Robert W., Can. J. Chem., 53(7), 1019–29 (English) 1975.*
Scholtissek, C.; Quack, G.; Klenk, H. D.; Webster, R. G., Antiviral Res., 37(2), 83–95 (English) 1998.*
Banks, Malcolm R.; Blake, Alexander J.; Cadogan, J. I. G.; Dawson, Ian M.; Gosney, Ian; Grant, Keith J.; Gaur, Suneel; Hodgson, Philip K. G.; Knight, Kevin S.; Smith, Glen W., Tetrahedron, 48(37), 7979–8006 (English) 1992.*
Kitahonoki, K.; Takano, Y., Takahashi, H., Tetrahedron, 24(12), 4605–23 (English) 1968.*
Alonso, et al., "(1S,3R,4R)–2–Azanorbornylmethanol, an Efficient Ligand for Ruthenium–Catalyzed Asymmetric Transfer Hydrogenation of Ketones", *J. Org. Chem.* 1998, 63, pp. 2749–2751.
Ninomiya, et al. "Phosphorous in Organic Synthesis —VII Diphenyl Phosphorazidate (DPPA). A New Convenient Reagent For A Modified Curtius Reaction", Tetrahedron, vol. 30, pp. 2151–2157 (1974).
Takano, et al. "IODO —And Phenylselenocarbamate Cyclizations: New Versatile Methods For Funtionalization of Olefinic Bonds", *Heterocycles,* vol. 19, No. 7, 1982, pp. 1243–1245.
Poll, et al. "Diastereoface–Discriminative Metal Coordination In Asymmetric Synthesis: D–Pantolactone As Practical Chiral Auxiliary For Lewis Acid Catalyzed Diels–Alder Reactions", Tetrahedron Letters, pp. 3095–3098, 1985.

* cited by examiner

Primary Examiner—Mukund J. Shah
Assistant Examiner—Thomas McKenzie
(74) Attorney, Agent, or Firm—Wenderoth, Lind & Ponack, L.L.P.

(57) ABSTRACT

Bicyclic amino alcohols, whose amino group and hydroxy group are bonded in positions 1,3 adjacent to the bridge, for example

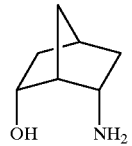

are valuable ligands for metal complexes of the d-8 metals of the periodic table of elements. The metal complexes in question are catalysts or catalyst precursors for the asymmetric hydrogenation or asymmetric transfer hydrogenation with hydrogen donors of prochiral organic compounds with carbon double bonds or carbon/hetero atom double bonds, for example ketones and imines.

5 Claims, No Drawings

BICYCLIC 1,3-AMINOALCOHOLS, D8-METAL COMPLEXES AND HYDROGENATION PROCESSES

The present invention relates to bicyclic aminoalcohols; metal complexes with d8-metals and bicyclic aminoalcohols as ligands; a process for the asymmetric transfer hydrogenation of prochiral carbon double bonds or hetero atom carbon bonds with alkanols as a source of hydrogen; the use of bicyclic aminoalcohols as ligands in d8-metal complexes; and the use of metal complexes with d8-metals and bicyclic aminoalcohols as ligands for the asymmetric transfer hydrogenation of prochiral carbon/carbon double bonds and hetero atom/carbon double bonds.

In CA-A-2.239.970, a process is described for the asymmetric hydrogenation of carbon-hetero atom double bonds in for example prochiral ketones or imines using inorganic or organic hydrogen donors, for example secondary alkanols, in which process transition metal complexes are used as enantioselective catalysts, which contain chiral nitrogen-containing compounds as ligands. In the entire description, only ligands having a 1,2-aminoethanol basic structure are mentioned. WO 98/42643 describes the same process, using the same or similar ligands, in which Ru, Rh and iridium complexes with cyclopentadienyl ligands are used as catalysts. In addition, open-chained 1,3-aminopropanols are mentioned as ligands, but only moderate optical yields can be attained with these.

In J. Org. Chem. (1998), 63, pages 2749 to 2751, D. A. Alonso et al also describe the said process, whereby 2-aza-1-hydroxymethylnorbornane is used as the bicyclic asymmetric ligand. This likewise has a 1,2-aminoethanol basic structure and the NH-group is additionally bonded in the norbornane ring. Using this ligand, high conversions and optical yields are obtained.

It has now surprisingly been found that, during the asymmetric transfer hydrogenation with asymmetric ligands of a 1,3-aminopropanol basic structure in metal complexes as catalysts, high conversions and optical yields may be attained when the optionally substituted OH and NH groups are bound in the vicinity of the bridge of an at least bicyclic ring system, and together with the metal atom, form a six-membered ring.

A first object of the invention is compounds of formula I in the form of the racemates thereof, mixtures of diastereoisomers or predominantly pure diastereoisomers,

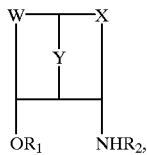

(I)

wherein

W signifies a direct bond or $C_1$–$C_4$-alkylene, X is a direct bond or $C_1$–$C_4$-alkylene, Y is $C_1$–$C_4$-alkylene, —O—, —S—, —$NR_3$—, —$NR_3$—$CHR_4$—, —$NR_3$—$CR_4R_5$, —$SiR_4R_5$—, —$CHR_4O$— or —$CR_4R_5O$—, $R_1$ signifies hydrogen, $C_1$–$C_6$-alkyl, $C_2$–$C_6$-alkenyl, $C_3$–$C_8$-cycloalkyl, $C_3$–$C_8$-cycloalkenyl, $C_6$–$C_{10}$-aryl, or $C_7$–$C_{12}$-aralkyl, $R_2$ is hydrogen, $C_1$–$C_6$-alkyl, $C_3$–$C_8$-cycloalkyl, $C_6$–$C_{10}$-aryl, or $C_7$–$C_{12}$-aralkyl, $C_1$–$C_8$-acyl, $C_1$–$C_6$-alkoxycarbonyl, $C_1$–$C_6$-alkylaminocarbonyl, di($C_1$–$C_6$-alkyl)aminocarbonyl, $(R_6)_2P(O)$—, or $R_6SO_2$—, $R_3$ signifies $C_1$–$C_6$-alkyl, cyclohexyl, phenyl or benzyl, $R_4$ and $R_5$, independently of one another, are $C_1$–$C_6$-alkyl, cyclohexyl, phenyl or benzyl, and $R_6$ is $C_1$–$C_6$-alkyl, $C_1$–$C_6$-halogenalkyl; or cyclohexyl, phenyl or benzyl either unsubstituted or substituted by $C_1$–$C_4$-alkyl, $C_1$–$C_4$-halogenalkyl, or $C_1$–$C_4$-alkoxy;

whereby aliphatic, saturated or ethylenically unsaturated and/or aromatic hydrocarbon rings are optionally condensed onto the rings of the bicyclic ring system; and the optionally condensed bicyclic ring system is unsubstituted or is substituted by $C_1$–$C_6$-alkyl, $C_1$–$C_6$-alkoxy, cyclohexyl, $C_6$–$C_{10}$-aryl, $C_7$–$C_{12}$-aralkyl, $C_1$–$C_4$-alkyl-$C_6$–$C_{10}$-aryl, $C_1$–$C_4$-alkoxy-$C_6$–$C_{10}$-aryl, $C_1$–$C_4$-alkyl-$C_7$–$C_{12}$-aralkyl, $C_1$–$C_4$-alkoxy-$C_7$–$C_{12}$-aralky;

as well as the acid addition salts thereof.

In formula I, W preferably signifies $C_1$–$C_3$-alkylene, and most preferably $C_1$- or $C_2$-alkylene. In formula I, X preferably signifies a direct bond or $C_1$–$C_3$-alkylene, most preferably $C_1$- or $C_2$-alkylene. In formula I, Y preferably signifies $C_1$- or $C_2$-alkylene. In an especially preferred embodiment, W, X and Y are selected so that in the bicyclic ring system of formula I they each form a 4- to 8-membered, preferably 5- to 7-membered, most preferably 5- or 6-membered hydrocarbon ring.

$R_1$ as alkyl preferably contains 1 to 4 C-atoms. Examples of alkyl are methyl, ethyl, n- and isopropyl, n—, iso- and tert.-butyl, as well as the isomers of pentyl and hexyl.

$R_1$ as alkenyl preferably contains 2 to 4 C-atoms. Examples of alkenyl are vinyl, allyl and crotonyl.

$R_1$ as cycloalkyl preferably contains 4 to 7 C-atoms. Examples of cycloalkyl are cyclopropyl, cyclobutyl, cyclopentyl, cyclohexyl, cycloheptyl and cyclooctyl. Cyclopentyl and cyclohexyl are preferred.

$R_1$ as cycloalkenyl preferably contains 4 to 7 C-atoms. Examples of cycloalkyl are cyclopropenyl, cyclobutenyl, cyclopentenyl, cyclohexenyl, cycloheptenyl and cyclooctenyl. Cyclopentenyl and cyclohexenyl are preferred.

$R_1$ as aryl may be for example phenyl or naphthyl.

$R_1$ as aralkyl may be for example phenyl-$C_1$–$C_4$-alkyl or naphthyl-$C_1$–$C_4$-alkyl. Benzyl and phenylethyl are preferred.

In a preferred embodiment, $R_1$ is hydrogen, $C_1$–$C_4$-alkyl, allyl, cyclopentyl, cyclohexyl, phenyl or benzyl. $R_1$ is most preferably hydrogen.

$R_2$ as alkyl preferably contains 1 to 4 C-atoms. Examples of alkyl are methyl, ethyl, n- and isopropyl, n-, iso- and tert.-butyl, as well as the isomers of pentyl and hexyl.

$R_2$ as cycloalkyl preferably contains 4 to 7 C-atoms. Examples of cycloalkyl are cyclopropyl, cyclobutyl, cyclopentyl, cyclohexyl, cycloheptyl and cyclooctyl. Cyclopentyl and cyclohexyl are preferred.

$R_2$ as aryl may be for example phenyl or naphthyl.

$R_2$ as aralkyl may be for example phenyl-$C_1$–$C_4$-alkyl or naphthyl-$C_1$–$C_4$-alkyl Benzyl and phenylethyl are preferred.

$R_2$ as alkoxycarbonyl is preferably $C_1$–$C_4$-alkoxycarbonyl. Examples of alkoxy are methoxy, ethoxy, n- and isopropyloxy, n-, iso- and tert.-butyloxy, as well as the isomers of pentyloxy and hexyloxy. $R_2$ is preferably tert.-butyloxycarbonyl.

When $R_2$ is the radical $(R_2)_2P(O)$— or $R_6$—$SO_2$—, $R_6$ is preferably $C_1$–$C_4$-alkyl, $C_1$–$C_4$-halogen-alkyl, or phenyl or benzyl either unsubstituted or substituted by methyl, ethyl, trifluoromethyl, methoxy or ethoxy. Halogen in the halogen moiety is preferably chlorine, and more preferably fluorine. Examples of the radical $R_6$—$SO_2$— are methyl-, ethyl-, n- and iso-propyl-, n- and iso-butyl-, phenyl-, benzyl-, methylphenyl-, ethylphenyl-, dimethylphenyl-, methylbenzyl-, dimethylbenzyl-, trifluoromethylphenyl- and bis(trifluormethyl)phenylsulfonyl. Examples of the radical $(R_6)_2P(O)-$ are dimethyl-, diethyl-, diphenyl- and di-p-toluyloxyphosphinyl.

If $R_2$ signifies acyl, it preferably contains 1 to 6, most preferably 1 to 4 C-atoms. A few examples are formyl, acetyl, propionyl, butyroyl and benzoyl.

If $R_2$ signifies alkylaminocarbonyl or di(alkyl) aminocarbonyl, the alkyl group preferably contains 1 to 4, most preferably 1 or 2 C-atoms. A few examples are methylamino-, dimethylamino-, ethylamino-, diethylamino-, methyl-ethylamino-, n- or iso-propylamino- and di-n- or -iso-propylaminocarbonyl If $R_3$ is alkyl, it preferably contains 1 to 4 C-atoms. $R_3$ is preferably ethyl and most preferably methyl.

If $R_4$ and $R_5$ are alkyl, it preferably contains 1 to 4 C-atoms. $R_4$ and $R_5$ are preferably methyl.

In a preferred embodiment, $R_2$ is $C_1$–$C_4$-alkyl, cyclopentyl, cyclohexyl, phenyl, benzyl, $C_1$–$C_4$-alkoxycarbonyl or the radical $R_6$–$SO_2$–, wherein $R_6$ is $C_1$–$C_4$-alkyl, $C_1$–$C_4$-fluoroalkyl, or phenyl either unsubstituted or substituted by one or two methyl or trifluoromethyl.

If hydrocarbon rings are condensed onto the bicyclic ring system, then these are preferably $C_6$–$C_{10}$-aryl (for example benzene or naphthaline), $C_3$–$C_8$-cycloalkyl, preferably $C_5$–$C_7$-cycloalkyl, or $C_4$–$C_8$-cycloalkenyl, preferably $C_5$–$C_7$-cycloalkenyl.

Preferred substituents for the optionally condensed bicyclic ring system are $C_1$–$C_4$-alkyl (for example methyl, ethyl, n- and iso-propyl and the isomers of butyl, and $C_1$–$C_4$-Alkoxy (for example methoxy, ethoxy, n- and iso-propyloxy and butyloxy), phenyl, benzyl, $C_1$–$C_2$-alkylphenyl.

Of the compounds according to the invention, those that are especially preferred are those of formula Ia,

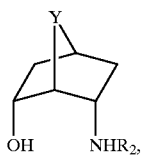

(Ia)

wherein Y signifies $-CH_2-$ or $-CH_2CH_2-$, and $R_2$ is H, $C_1$–$C_4$-alkyl (especially methyl or ethyl), or the radical of formula $R_6$–$SO_2$–, and $R_6$ is $C_1$–$C_4$-alkyl (especially methyl or ethyl), phenyl or phenyl (for example p-toluyl), which is substituted by $C_1$–$C_4$-alkyl (especially methyl or ethyl) or by trifluoromethyl.

Acids for the formation of acid addition salts may be selected from inorganic and organic acids. Examples of organic acids are carboxylic acids, phosphonic acids and sulfonic acids, such as formic acid, acetic acid, fluoroacetic acids, chloroacetic acids, propionic acid, oxalic acid, malonic acid, benzoic acid, methylphosphonic acid, phenylphosphonic acid, p-toluyl-phosphonic acid, methylsulfonic acid, trifluoromethylsulfonic acid, phenylsulfonic acid and p-toluylsulfonic acid. Examples of organic acids are hydrohalic acids, especially HCl, HBr and HI, sulphuric acid, phosphorous acid, phosphoric acid, tetrafluoroboric acid and hexafluorophosphoric acid.

The compounds according to the invention may be produced from known unsaturated bicyclic carboxylic acids or those produced according to known or analogous methods.

A further object of the invention is a process for the preparation of compounds of formula I, which is characterised in that (a) a compound of formula II

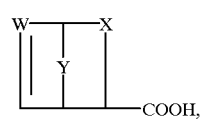

(II)

wherein W, X and Y are defined as indicated above, is reacted with a phosphoric acid ester azide in the presence of an alcohol R—OH, wherein R signifies $C_1$–$C_6$-alkyl, $C_5$–$C_8$-cycloalkyl, $C_5$–$C_8$-cycloalkyl-$C_1$–$C_4$-alkyl, benzyl, or benzyl substituted by $C_1$–$C_4$-alkyl, to form a compound of formula III,

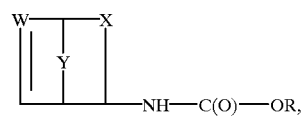

(III)

b) the compound of formula III is cyclised with bromine, iodine or an electrophilic brominating or iodising agent to form a compound of formula IV, wherein X' is Br or I,

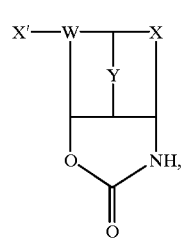

(IV)

c) in the compound of formula IV, the halogen is substituted by hydrogen to form a compound of formula V,

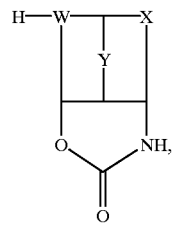

(V)

d) the compound of formula V is hydrolysed or reduced to the compound of formula VI,

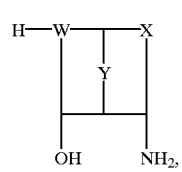

(VI)

e) or in the compound of formula V, the hydrogen atom of the NH group is substituted by the group R'$_2$ to form compounds of formula VII, wherein R'$_2$ signifies C$_1$–C$_6$-alkyl, C$_3$–C$_8$-cycloalkyl, C$_6$–C$_{10}$-aryl, or C$_7$–C$_{12}$-aralkyl, and then the compounds of formula VII are hydrolysed or reduced to compounds of formula VIII,

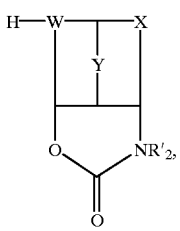

(VII)

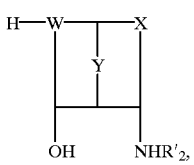

(VIII)

f) or the compounds of formula VI are reacted with C$_1$–C$_6$-alkoxycarbonates, C$_1$–C$_6$-alkylamino- or C$_1$–C$_6$-dialkylamino-carbonyl halides, C$_1$–C$_8$-carboxylic acid halides, C$_1$–C$_6$-alkoxycarbonyl halides, (R$_6$)$_2$P(O)-halides or R$_6$—SO$_2$— esters or halides, to form compounds of formula IX, wherein R"$_2$ signifies C$_1$–C$_6$-alkoxycarbonyl, C$_1$–C$_8$-acyl, C$_1$–C$_6$-alkylamino-, C$_1$–C$_6$-dialkylaminocarbonyl or the groups (R$_6$)$_2$P(O)— und R$_6$—SO$_2$—.

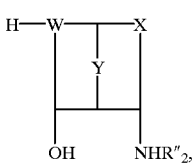

(IX)

g) and in compounds of formulae VI, VII and IX, the OH group is etherified to compounds of formula X, R', signifies C$_1$–C$_6$-alkyl, C$_2$–C$_6$-alkenyl, C$_3$–C$_8$-cycloalkyl, C$_3$–C$_8$-cycloalkenyl, C$_6$–C$_{10}$-aryl, or C$_7$–C$_{12}$-aralkyl, and R$_2$ is defined as indicated for formula I,

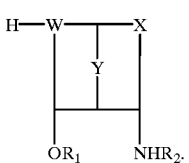

(X)

Another object of the invention is compounds of formula V, which are valuable intermediates in the preparation of the compounds according to the invention,

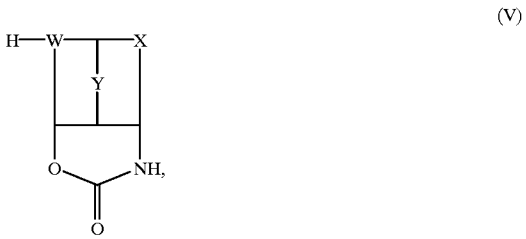

(V)

wherein W, X and Y are defined as indicated for formula I, whereby aliphatic, saturated or ethylenically unsaturated and/or aromatic hydrocarbon rings are optionally condensed onto the rings of the bicyclic ring system; and
the optionally condensed bicyclic ring system is unsubstituted or is substituted by C$_1$–C$_6$-alkyl, C$_1$–C$_6$-alkoxy, cyclohexyl, C$_6$–C$_{10}$-aryl, C$_7$–C$_{12}$-aralkyl, C$_1$–C$_4$-alkyl-C$_6$–C$_{10}$-aryl, C$_1$–C$_4$-alkoxy-C$_6$–C$_{10}$-aryl, C$_1$–C$_4$-alkyl-C$_7$–C$_{12}$-aralkyl or C$_1$–C$_4$-alkoxy-C$_7$–C$_{12}$-aralkyl.

The reaction (Curtius reaction) of process step a) is known per se and is described by K. Ninomiya et al. in Tetrahedron Vol. 30, pages 2151–2157 (1974). Details are given in the examples.

The reaction of process step b) is likewise known and is described by S. Takano et al. in Heterocyles Vol. 19, No. 7, pages 1243–1245 (1982). Known electrophilic halogenation agents are for example N—Br— or N—I-carboxylic acid and -sulfonic acid imides (N—Br— or N—I—succinimide). Details are given in the examples.

The reaction of process step c) is generally known. The substitution by hydrogen may be carried out with metal hydrides and is preferably carried out catalytically with hydrogen in the presence of noble metal catalysts.

The hydrolysis of process steps d) and e) is a generally known reaction which is familiar to a person skilled in the art and which uses aqueous acids or aqueous bases. Metal hydrides are preferably used for reduction, for example LiAlH$_4$.

The formation of secondary amines in process step e) by substitution of a hydrogen atom in the NH$_2$ group is a reaction that has been known for a long time. Substitution reagents that are primarily employed are hydrocarbon chlorides, bromides and iodides.

The preparation of the compounds of formula IX in process step f by means of amino-carbonylation, alkoxycarbonylation, acylation, phosphorylation or sulfonation is similarly a reaction which has been known for a long time and which is described more fully in the examples. The etherification of process step g) by means of alkylation agents such as alkyl halides or alkyl sulfates is also generally known and is not described in detail here.

Compounds of formula I, in which R$_2$ is methyl, are also obtainable by reduction of carbamoyl compounds of formula IX, in which R"$_2$ signifies C$_1$–C$_6$-alkoxycarbonyl. The reduction agents used are suitably metal hydrides, such as LiAlH$_4$.

Addition salts are obtained in a simple manner, by reacting compounds of formula I with acids in equimolar amounts.

Diastersoisomeric mixtures and pure diastereoisomers may be obtained by the usual separation processes, if they have not already been formed during synthesis. Conventional separation processes are crystallisation and chromatography.

The reactions of process steps a) to g) may be carried out without or in the presence of an inert solvent, whereby one solvent or mixtures of solvents may be used. Suitable solvents are, for example, aliphatic, cycloaliphatic and aromatic hydrocarbons (pentane, hexane, petroleum ether, cyclohexane, methylcyclohexane, benzene, toluene, xylene), aliphatic halogen-hydrocarbons (methylene chloride, chloroform, di- and tetrachloroethane), nitriles (acetonitrile, propionitrile, benzonitrile), ethers (diethylether, dibutylether, tert.-butylmethylether, ethylene glycol dimethylether, ethylene glycol diethylether, diethylene glycol dimethylether, tetrahydrofuran, dioxane, diethylene glycol monomethyl- or monoethylether), ketones (acetone, methyl isobutyl ketone), carboxylates and lactones (ethyl and methyl acetate, valerolactone), N-substituted lactams (N-methylpyrrolidone), carboxamides (dimethylamide, dimethylformamide), acyclic ureas (dimethyl imidazoline), and sulfoxides and sulfones (dimethyl sulfoxide, dimethyl sulfone, tetramethylene sulfoxide, tetramethylene sulfone) and alcohols (methanol, ethanol, propanol, butanol, ethylene glycol monomethyl ether, ethylene glycol monoethyl ether, diethylene glycol monomethyl ether) and water. The solvents may be used on their own or in a mixture of at least two solvents.

The reaction may be carried out whilst cooling, for example to −30° C., at room temperature or at elevated temperature, for example 30 to 250° C. Normally, equimolar amounts of the reactants are used, or an excess of one reactant. Isolation of the reaction products may be effected for example by distillation, crystallisation and/or extraction; and the products may be purified by distillation, recrystallisation and/or chromatography.

The compounds of formula I according to the invention are excellent ligands for metal complexes of the d8 metals of the periodic table of elements, which can be used as catalysts or precursors of catalysts, especially during hydrogenation and transfer hydrogenation using hydrogen donors. If prochiral unsaturated compounds are used, a high excess of optical isomers can be induced in the synthesis of organic compounds and a high chemical conversion can be achieved.

A further object of the invention is metal complexes of metals selected from the secondary group VII of the periodic table of elements with compounds of formula I as ligands. The selected metals within the context of the invention are also called d-8 metals.

Depending on the oxidation number and coordination number of the metal atom, the metal complexes may contain further ligands and/or anions. The metal complexes in question may also be cationic metal complexes. Analogous metal complexes of this type, and the preparation thereof (in situ or as isolated compounds), have been described in literature many times (see for example A. Fujii et al., JACS, 118, (1996), 2521 ff. and J. Takehara et al., Chem. Communication (Cambridge), as well as CA-A-2,239,970 and WO 98/42643).

The ligands according to the invention may exist in the metal complexes as neutral ligands or as ionic amide ligands. In addition, the metal complexes may contain identical or different, monodentate or bidentate, anionic or non-ionic ligands. They may also be complex salts with anions of an oxyacid or complex acid. Anions and anionic ligands serve to balance the charge of the oxidation stages of the metal.

The d8 metal may be selected from the group Fe, Ni, Co, Rh, Pd, Ir, Ru and Pt, and preferably from the group Rh, Ir and Ru, the metal having the oxidation degrees 0, 1, 2, 3 or 4.

The above-described preferences and embodiments apply to the compounds of formula I.

Monodentate non-ionic ligands may be selected for example from the group of olefins (for example ethylene, propylene), solvatising solvents (nitriles, linear or cyclic ethers, optionally N-alkylated amides and lactams, amines, phosphines, alcohols, carboxylic acid esters, sulfonic acid esters), nitrogen monoxide and carbon monoxide.

Further non-ionic (neutral) ligands are arenes with for example 6 to 18 carbon atoms. The arenes in question may be monocycles or condensed ring systems. The arenes preferably contain 6 to 14, most preferably 6 to 10 carbon atoms. The arenes may be unsubstituted or substituted, for example by $C_1$–$C_4$-alkyl, $C_1$–$C_4$-alkoxy, $C_1$–$C_4$-fluoroalkyl, $C_1$–$C_4$-hydroxyalkyl, hydroxyl, halogen, cyano, —$CO_2H$, —$SO_3H$, carboxy-$C_1$–$C_4$-alkyl or carbamide.

Arenes preferably contain 6 to 18, more preferably 6 to 14, most preferably 6 to 10 carbon atoms. They may be unsubstituted or substituted by $C_1$–$C_6$-alkyl, $C_1$–$C_8$-alkoxy or halogen. A few examples of arenes and heteroarenes are benzene, naphthalene, anthracene, indan, fluorene, biphenyl, indan, toluene, hexamethylbenzene, 1,3,5-mesitylene and cumene.

Monodentate anionic ligands may be selected for example from the group hydride, halide (F, Cl, Br, I), pseudohalide (cyanide, cyanate, isocyanate) and anions of carboxylic acids, sulfonic acids, phosphonic acids (carbonate, formate, acetate, propionate, methylsulfonate, trifluoromethylsulfonate, phenylsulfonate, tosylate), allyls (allyl, 2-methallyl), and optionally substituted cyclopentadienylene (cyclopentadienyl, methylcyclopentadienyl, dimethyl-cyclopentadienyl, trimethylcyclopentadienyl, tetramethylcyclopentadienyl, penta-methyl-cyclopentadienyl, trimethylsilylcyclopentadienyl, indenyl).

Bidentate non-ionic ligands may be selected for example from the group of linear or cyclic diolefins (for example hexadiene, cyclohexadiene, cyclooctadiene, norbornadiene), dinitriles (malonodinitrile), optionally N-alkylated dicarboxylic acid diamides, diamines, diphosphines, diols, acetonyl acetonates, dicarboxylic acid diesters, disulfonic acid diesters and amino-alcohols.

Bidentate anionic ligands may be selected for example from the group of anions of dicarboxylic acids, disulfonic acids, diphosphonic acids (for example oxalic acid, malonic acid, succinic acid, maleic acid, methylenedisulfonic acid and methylenediphosphonic acid) and bridged cyclopentadienylene [methylene-biscyclopentadienyl, methylene-bis-(tetramethylcyclopentadienyl), biscyclopentadienyl-dimethylsilane)].

Preferred metal complex salts are those with anions selected from the group Cl, Br, I, $ClO_4^-$, $CF_3SO_3^-$, $CH_3SO_3^-$, $HSO_4^-$, $BF_4^-$, $B(phenyl)_4^-$, $PF_6^-$, $SbCl_6^-$, $AsF_6^-$, $SbF_6^-$ or $B(3,5\text{-}CF_3\text{–}C_6H_5)_4^-$.

A preferred group of metal complexes comprises those of formula XI,

$$[Ru(arene)(L)(A)] \qquad (XI),$$

wherein A is hydride or chloride, and L signifies a ligand of formula I. The above-mentioned embodiments and preferences apply to arene.

Another preferred group of metal complexes comprises those of formula XII,

$$[Me(diene)(L)(A_1)] \qquad (XII),$$

wherein Me is Rh or Ir, diene signifies an open-chained or cyclic diene, L represents a ligand of formula I, and $A_1$ signifies halide, preferably chloride, bromide or iodide. The above-mentioned embodiments and preferences apply to diene and the ligands of formula I. The complexes of formula XII are obtainable by reacting the ligand L with [Me(diene)A$_1$)]$_2$.

A further preferred group of metal complexes comprises those of formula XIII, $$[Me_1Cp(L)A_2] \quad (XIII),$$

wherein Me$_1$ signifies Rh, Ir or Ru, A$_2$ is hydride or halide, preferably chloride, L signifies a ligand of formula I, and Cp represents an optionally substituted cyclopentadienyl or indenyl. The above-mentioned embodiments and preferences apply to the ligands of formula I and cyclopentadienyls as well as indenyls. The complexes of formula XIII are obtainable by reacting the ligand L with [Me$_1$CpA$_1$)]$_2$.

The metal complexes according to the invention are prepared by methods known in literature (see also CA-A-2,239,970 and WO 98/42643).

The metal complexes according to the invention are homogeneous catalysts or are catalyst precursors that can be activated under the reaction conditions, and they may be used for example for the hydrogenation of unsaturated organic compounds.

The metal complexes are preferably used for the asymmetric hydrogenation of prochiral compounds with carbon/carbon or carbon/hetero atom multiple bonds, in particular double bonds. The metal complexes are especially suitable for transfer hydrogenation using hydrogen donors. Hydrogenation of this kind with soluble homogeneous metal complexes is described for example in Pure and Appl. Chem., Vol. 68, No. 1, pp. 131–138 (1996).

A further object of the invention is therefore the use of the metal complexes according to the invention as homogeneous catalysts for hydrogenation, preferably transfer hydrogenation with hydrogen donors, of prochiral compounds having carbon/carbon or carbon/hetero atom multiple bonds, especially carbon/hetero atom double bonds.

A further aspect of the invention is a process for the asymmetric hydrogenation with hydrogen, or transfer hydrogenation with hydrogen donors, of prochiral compounds with carbon- or carbon/hetero atom multiple bonds, especially carbon/hetero atom double bonds, which is characterised in that the compounds are reacted at low to elevated temperatures in the presence of catalytic quantities of a metal complex according to the invention.

Preferred prochiral, unsaturated compounds to be hydrogenated may contain one or more, identical or different groups C=C, C=N and/or C=O, in open-chained or cyclic organic compounds, whereby the groups C=C, C=N and/or C=O may be part of a ring system or may represent exocyclic groups. The prochiral, unsaturated compounds in question may be alkenes, cycloalkenes, heterocycloalkenes, and also open-chained or cyclic ketones, ketimines and ketohydrazones. They may correspond, for example, to formula XIV, $$R_7R_8C{=}D \quad (XIV),$$

wherein R$_7$ and R$_8$ are selected in such a way that the compound is prochiral, and, independently of one another, represent an open-chained or cyclic hydrocarbon radical or hetero-hydrocarbon radical with hetero atoms selected from the group O, S and N, containing 1 to 30, preferably 1 to 20 carbon atoms;

D is O or a radical of formula C=R$_9$R$_{10}$ or NR$_{11}$;

R$_9$ and R$_{10}$, independently of one another, have the same significance as R$_7$ and R$_8$;

R$_{11}$, signifies hydrogen, C$_1$–C$_{12}$-alkyl, C$_1$–C$_{12}$-alkoxy, C$_3$–C$_{12}$-cycloalkyl, C$_3$–C$_{12}$-cycloalkyl-C$_1$–C$_6$-alkyl, C$_3$–C$_{11}$-heterocycloalkyl, C$_3$–C$_{12}$-heterocycloalkyl-C$_1$–C$_6$-alkyl, C$_6$–C$_{14}$-aryl, C$_5$–C$_{13}$-hetero-aryl, C$_7$–C$_{16}$-aralkyl or C$_6$–C$_{14}$-heteroaralkyl;

R$_7$ and R$_8$, together with the carbon atom to which they are bonded, form a hydrocarbon ring or hetero-hydrocarbon ring with 3 to 12 ring members;

R$_7$ and R$_9$, together with the C=C-group to which they are bonded, each form a hydrocarbon ring or hetero-hydrocarbon ring with 3 to 12 ring members;

R$_7$ and R$_{11}$, together with the C=N-group to which they are bonded, each form a hydrocarbon ring or hetero-hydrocarbon ring with 3 to 12 ring members; the hetero atoms in the heterocyclic rings are selected from the group O, S and N; and R$_7$, R$_8$, R$_9$, R$_{10}$ and R$_{11}$ are unsubstituted or substituted by C$_1$–C$_6$-alkyl, C$_1$–C$_6$-alkoxy, cyclohexyl, C$_6$–C$_{10}$-aryl, C$_7$–C$_{12}$-aralkyl, C$_1$–C$_4$-alkyl-C$_6$–C$_{10}$-aryl, C$_1$–C$_4$-alkoxy-C$_6$–C$_{10}$-aryl, C$_1$–C$_4$-alkyl-C$_7$–C$_{12}$-aralkyl, C$_1$–C$_4$-alkoxy-C$_7$–C$_{12}$-aralkyl, —OH, —CO—OR$_7$, —CO—NR$_8$R$_9$ or —NR$_8$R$_9$, wherein R$_7$ is H, an alkali metal, C$_1$–C$_6$-alkyl, cyclohexyl, phenyl or benzyl, and R$_8$ and R$_9$, independently of one another, are hydrogen, C$_1$–C$_6$-alkyl, cyclohexyl, phenyl or benzyl, or R$_8$ and R$_9$ together signify tetramethylene, pentamethylene or 3-oxapentylene.

Examples and preferences of substituents have already been mentioned.

R$_7$ and R$_8$ may be for example C$_1$–C$_{20}$-alkyl, and preferably C$_1$–C$_{12}$-alkyl, C$_1$–C$_{20}$-heteroalkyl and preferably C$_1$–C$_{12}$-heteroalkyl with hetero atoms selected from the group O, S and N, C$_3$–C$_{12}$-alkyl and preferably C$_4$–C$_8$-cycloalkyl, C-bonded C$_3$–C$_{11}$-heterocycloalkyl and preferably C$_4$–C$_8$-heterocycloalkyl with hetero atoms selected from the group O, S and N, C$_3$–C$_{12}$-cycloalkyl-C$_1$–C$_6$-alkyl and preferably C$_4$–C$_8$-cycloalkyl-C$_1$–C$_6$-alkyl, C$_3$–C$_{11}$-heterocycloalkyl-C$_1$–C$_6$-alkyl and preferably C$_4$–C$_8$-heterocycloalkyl-C$_1$–C$_6$-alkyl with hetero atoms selected from the group O, S and N, C$_6$–C$_{14}$-aryl and preferably C$_6$–C$_{10}$-aryl, C$_5$–C$_{13}$-heteroaryl and preferably C$_5$–C$_9$-heteroaryl with hetero atoms selected from the group O, S and N, C$_7$–C$_{15}$-aralkyl and preferably C$_7$–C$_{11}$-aralkyl, C$_6$–C$_{12}$-hetero-aralkyl and preferably C$_6$–C$_{10}$-heteroaralkyl with hetero atoms selected from the group O, S and N.

When R$_7$ and R$_8$, R$_7$ and R$_9$, or R$_7$ and R$_{11}$ each together form a hydrocarbon ring or hetero-hydrocarbon ring, the ring preferably contains 4 to 8 ring members. The hetero-hydrocarbon ring may contain for example 1 to 3, preferably one or two hetero atoms.

In formula XIV, D is preferably the radical NR$_{11}$, most preferably O.

R$_{11}$ preferably signifies hydrogen, C$_1$–C$_6$-alkyl, C$_1$–C$_6$-alkoxy, C$_4$–C$_8$-cycloalkyl, C$_4$–C$_8$-cycloalkyl-C$_1$–C$_4$-alkyl, C$_4$–C$_{10}$-heterocycloalkyl, C$_4$–C$_{10}$-heterocycloalkyl-C$_1$–C$_4$-alkyl, C$_6$–C$_{10}$-aryl, C$_5$–C$_9$-heteroaryl, C$_7$C$_{12}$-aralkyl and C$_5$–C$_{13}$-heteroaralkyl.

A few examples of prochiral ketones are acetophenone, 4-methoxyacetophenone, 4-tri-fluoromethylacetophenone, 4-nitroacetophenone, 2-chloroacetophenone, corresponding acetophenone benzylimines, unsubstituted or substituted benzocyclohexanone or benzocyclopentanone, and imines from the group unsubstituted or substituted tetrahydroquinoline, tetrahydropyridine and dihydropyrrole.

Hydrogen donors are, for example, primary and secondary alcohols, primary and secondary amines, carboxylates, carboxylic acids and their ammonium salts, readily dehydrogenatable hydrocarbons and reduction agents. The hydrogen donors are used in at least equimolar amounts or in an excess, based on the compound to be hydrogenated. The excess may be up to 5 mols and more, especially if suitable hydrogen donors serve as solvents at the same time. Hydrogen donors may be used in a mixture with additional hydrogen.

The primary and secondary alcohols preferably contain 1 to 10 carbon atoms, more preferably 2 to 6 carbon atoms, and most preferably 3 or 4 carbon atoms. A few examples are methanol, ethanol, n- and isopropanol, n- and isobutanol, 1-, 2- or 3-pentanol, 1-, 2- or 3-hexanol, cyclopentanol, cyclohexanol, benzyl alcohol and menthol. Secondary alcohols are preferred, particularly isopropanol and isobutanol.

The primary and secondary amines may contain, for example, 1 to 20 carbon atoms, preferably 2 to 16 carbon atoms, most preferably 3 to 12 carbon atoms. A few examples are ethylamine, n- and isopropylamine, n- and isobutylamine, pentylamine, hexylamine, benzylamine, piperidine, morpholine, cyclohexylamine, diethylamine, di-n- or -isopropyl-amine, di-n- or -isobutylamine, dipentylamine and dihexylamine. Primary amines are preferred, especially primary amines with a branched alkyl group, for example isopropylamine and isobutylamine.

The carboxylic acids are preferably aliphatic or cycloaliphatic carboxylic acids, with for example 1 to 10 carbon atoms, preferably 1 to 4 carbon atoms. They may be substituted by hydroxyl groups, especially in beta-position to the carboxyl group. A few examples are formic acid, lactic acid and ascorbic acid. Carboxylates may be derived from the above-mentioned carboxylic acids, and contain for example a $C_1-C_{20}$-alkyl group, preferably $C_1-C_4$-alkyl group in the ester group.

The ammonium salts may be derived from the above-mentioned carboxylic acids and primary, secondary, tertiary or quaternary ammonium. The ammonium may contain for example 1 to 20, preferably 2 to 16, most preferably 3 to 12 carbon atoms. Tri($C_1-C_4$-alkyl)ammonium is especially suitable. A few examples of ammonium are methylammonium, dimethylammonium, trimethylammonium, ethylammonium, diethylammonium, triethylammonium, methylethylammonium, isopropyldiethylamine, di-isopropylethylamine. Trialkylammonium formate, especially triethyl formate, are preferred in particular. The molar ratio of carboxylic acid to amine in the reaction mixture is in general approximately 5 to 2.

Readily dehydrogenatable hydrocarbons are for example those that have a tendency to aromatise or to form conjugated systems. A few examples are cyclohexadiene, cyclohexene, tetraline, dihydrofuran and terpene.

Suitable reduction agents are for example hydrazine and hydroxylamine.

Low to elevated temperature in the context of the invention can mean for example −20 to 150° C., preferably −10 to 100° C., most preferably 10 to 80° C. The optimum yields are generally better at lower temperature than at higher temperatures. In hydrogenation, the hydrogen pressure may be for example from $10^5$ to $2×10^7$ Pa (Pascal). Transfer hydrogenation is preferably carried out at normal pressure or slight excess pressure.

Catalysts are preferably used in amounts of 0.0001 to 10 mol %, more preferably 0.001 to 10 mol %, most preferably 0.01 to 5 mol %, based on the compound to be hydrogenated.

The reaction can be carried out without solvents or in the presence of inert solvents. Solvents are generally known, and the choice thereof depends primarily on the solubility of the substrate and metal complexes. Suitable solvents have already been named.

The reaction may take place in the presence of bases. Suitable bases are, for example, alkali and alkaline earth bases [LiOH, NaOH, KOH, Mg(OH)$_2$ and Ca(OH)$_2$] alkali metal alcoholates of $C_1-C_6$-alkanols (lithium, sodium, potassium, cesium methylate, ethylate, -n- and -isopropylate, -n-, -iso- and -t-butylate), alkali metal carbonates (Li$_2$CO$_3$, Na$_2$CO$_3$, K$_2$CO$_3$, KHCO$_3$) and alkali metal carboxylates of $C_1-C_6$-carboxylic acids (formates, acetates, propionates and butyrates). The molar ratio of catalyst metal to base is, for example, from 1:1 to 1:4, preferably 1:1 to 1:2.

The metal complexes used as catalysts may be added as separately produced, isolated compounds, or may also be formed in situ prior to the reaction and then mixed with the substrate to be hydrogenated.

Hydrogenation may be carried out continuously or intermittently in various types of reactor. Preference is given to those reactors which allow propitious blending and good heat removal, e.g. loop reactors. This type of reactor has proved favourable especially when using small amounts of catalyst.

The hydrogenated organic compounds which may be produced according to the invention are active substances or intermediates in the preparation of such substances, especially in the preparation of pharmaceuticals and agrochemicals. Thus for example o,o-dialkylarylketamine derivatives, especially those with alkyl and/or alkoxyalkyl groups, are effective as fungicides, especially as herbicides. The derivatives in question may be amine salts, acid amides, e.g. of chloroacetic acid, tertiary amines and ammonium salts (see e.g. EP-A-0 077 755 and EP-A-0 115 470).

The following examples illustrate the invention.

A) Preparation of Ligands

EXAMPLE A1

Preparation of 1-amino-3-hydroxy-norbornane (A1)

a) Preparation of (a)

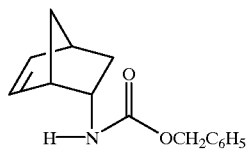

18 g of (−)(1S,2S)-5-norbornene-2-carboxylic acid are dissolved in 360 ml of toluene. After adding 19.1 ml of triethylamine and 31 ml of phosphoric acid diphenylester azide, stirring is effected for 30 minutes at room temperature. Subsequently, 16.1 ml of benzyl alcohol are added. The reaction mixture is stirred under reflux for 17 hours and then cooled to room temperature. After adding 350 ml of toluene, the mixture is washed twice with saturated aqueous NaCl solution, dried over MgSO$_4$ and concentrated by evaporation on a rotary evaporator. From the residue, the title compound (a) is obtained in the form of an oil by flash chromatography (SiO$_2$ 60F/ethyl acetate/hexane, 1:5) (16.2 g, 51% of theory). $^1$H-NMR (400 Hz, DMSO$_{d6}$) δ: 0.82 (1H); 1.30 (2H); 2.0 (1H); 2.77 (1H); 3.0 (1H); 4.0 (1H); 5.0 (2H); 5.95 (1H); 6.25 (1H); 6.82 (1H); 7.35 (5H).

b) Preparation of

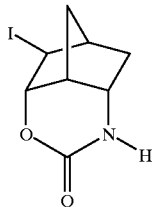

(b)

15.85 g of (a) are dissolved in 180 ml of dichloromethane, mixed with 19.84 g of iodine and subsequently stirred for 1 hour at room temperature. The reaction mixture is diluted with 1 liter of ethyl acetate, washed with aqueous sodium bisulfite solution (2×) and water (1×), dried over $MgSO_4$ and then concentrated by evaporation on a rotary evaporator. The residue is mixed with 200 ml of tert.-butylmethylether and stirred for 15 minutes at room temperature. The mixture is filtered, washed with tert.-butylmethylether (2×), to produce the title compound (b) as a yellow solid (15.9 g, 87% of theory). $^1$H-NMR (400 Hz, $CDCl_3$) δ: 1.47 (1H); 1.70 (1H); 2.15 (2H); 2.45 (1H); 2.65 (1H); 3.85 (1H); 3.90 (1H); 5.21 (1H); 6.52 (1H).

c) Preparation of

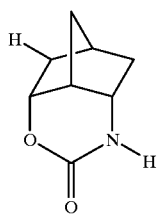

(c)

15.5 g of (b) are dissolved in 450 ml of ethanol, and after adding 14 ml of triethylamine and 0.9 g of $PtO_2,H_2O$, are hydrogenated at normal pressure. After 2 hours, the reaction mixture is filtered and concentrated by evaporation on a rotary evaporator. The residue is dissolved in 500 ml of dichloromethane, washed with saturated aqueous sodium bicarbonate solution (1×) and with saturated aqueous NaCl solution (1×), dried over $MgSO_4$ and then concentrated by evaporation on a rotary evaporator. From the residue, the title compound (c) is obtained as a light beige solid by flash chromatography ($SiO_2$ 60F/dichloromethane/methanol, 15:1) (6.2 g, 73% of theory). $^1$H-NMR (400 Hz, $CDCl_3$) δ: 1.40 (2H); 1.50 (2H); 2.08 (1H); 2.15 (2H); 2.43 (1H); 3.81 (1H); 4.82 (1H); 6.35 (1H).

d) Preparation of Compound A1

19 g of (c) are dissolved in 450 ml of ethanol, mixed with 250 ml of 4N aqueous sodium hydroxide solution and subsequently stirred under reflux for 24 hours. The ethanol is concentrated by evaporation on a rotary evaporator and then the aqueous phase is extracted with 500 ml of dichloromethane. The aqueous phase is separated and again extracted with dichloromethane (2×). The combined organic phases are washed with saturated aqueous NaCl solution (1×), dried over $MgSO_4$ and concentrated by evaporation on a rotary evaporator. From the residue, the title compound A1 is obtained as a white solid by flash chromatography ($SiO_2$ 60F/dichloromethane/methanol/$NH_3$, 40:10:1) (11.86 g, 75% of theory).

EXAMPLE A2

Preparation of 1-amino-3-hydroxy-norbornane Hydrochloride 1 g of A1 is dissolved in 10 ml of ethanol and mixed at room temperature with 10 ml of 15% HCl in ethanol. After concentrating by evaporation on a rotary evaporator, a white solid is obtained (1.359), which is recrystallised from 22 ml of isopropanol. The title compound A2 is thus obtained as a white solid (0.86 g, 67% of theory). Melting point >220° C.; $^1$H-NMR (400 Hz, $DMSO_{d6}$) δ: 1.13 (1H); 1.32 (3H); 2.08 (2H); 2.21 (1H); 2.41 (1H); 3.55 (1H); 4.40 (1H); 7.70 (3H).

EXAMPLE A3

Preparation of 1-t-butyloxycarbonylamino-3-hydroxy-norbornane (A3)

1 g of A1 is dissolved in 5 ml of dichloromethane and mixed with 1.75 ml of ethyl-diisopropyl-amine whilst cooling with ice. Subsequently, a solution of 1.89 g of di-tert.-butyl dicarbonate in 10 ml of dichloromethane is dispensed in. The white suspension is stirred for 18 hours at room temperature and subsequently concentrated on a rotary evaporator. The residue is mixed with 50 ml of ethyl acetate, washed with water (1×) and saturated aqueous NaCl solution (1×), dried over $MgSO_4$ and concentrated by evaporation on a rotary evaporator. From the residue, the title compound A3 is obtained as a white solid by flash chromatography ($SiO_2$ 60F/dichloromethane/methanol, 30:1) (1.45 g, 83%): $^1$H-NMR (400 Hz, $DMSO_{d6}$) δ: 1.0 (2H); 1.27 (2H); 1.40 (9H); 2.05 (2H); 2.18 (2H); 3.95 (1H); 4.30 (1H); 5.52 (1H); 7.12 (1H).

EXAMPLE A4

Preparation of 1-methylamino-3-hydroxy-norbornane (A3)

A solution of 1.4 g of A3 in 15 ml of tetrahydrofuran is dispensed into a suspension of 0.96 g of lithium aluminium hydride in 20 ml of tetrahydrofuran whilst cooling with ice. When this addition is complete, the reaction mixture is firstly heated to room temperature and then stirred under reflux for 18 hours. Then, 10 ml of 2N sodium hydroxide solution are dispensed in whilst cooling with ice. The white suspension is filtered and the filtrate concentrated by evaporation on a rotary evaporator. The residue is dissolved in 20 ml of diethylether, washed with saturated aqueous NaCl solution (1×), dried over $MgSO_4$ and concentrated by evaporation on a rotary evaporator. From the residue, the title compound A3 is obtained as a colourless oil by bulb tube distillation (90° C., 0.03 mbars) (0.45 g, 50% of theory).

EXAMPLE A4

Preparation of 1-methylamino-3-hydroxy-norbornane Hydrochloride (A4)

0.4 g of A3 are dissolved in 4 ml of ethanol and mixed at room temperature with 4 ml of 15% HCl in ethanol. After concentrating by evaporation on a rotary evaporator, a white solid is obtained (0.44 g), which is recrystallised from 2 ml of isopropanol. The title compound A4 is thus obtained as a white solid (0.2 g, 40%). Melting point 154° C. $^1$H-NMR (400 Hz, $DMSO_{d6}$) δ: 1.13 (1H); 1.38 (3H); 2.05 (2H); 2.25 (1H); 2.52 (3H); 3.43 (1H); 4.35 (1H); 5.92 (1H); 8.57 (2H).

EXAMPLE A5

Preparation of 1-p-toluenesulfonylamino-3-hydroxy-norbornane (A5)

0.7 g of A1 are dissolved in 7 ml of dichloromethane and mixed with 0.9 ml of pyridine. 1.05 g of p-toluenesulfochloride are added whilst cooling with ice, and the reaction mixture is stirred for 2 hours. The mixture is diluted with 50 ml of dichloromethane, washed with water (1×), dried over $MgSO_4$ and concentrated by evaporation on a rotary evaporator. From the residue, the title compound A5 is obtained as a white solid by flash chromatography ($SiO_2$ 60F/dichloromethane/methanol 20:1) and subsequent recrystallisation from toluene (0.53 g, 35% of theory). Melting point: 110–111° C. $^1$H-NMR (400 Hz, $DMSO_{d6}$) δ: 0.92 (2H); 1.14 (2H); 1.90 (4H); 2.40 (3H); 3.70 (1H); 4.22 (1H); 5.72 (1H); 7.40 (2H); 7.50 (1H); 7.70 (2H).

EXAMPLE A6

Preparation of A1 a) Preparation of

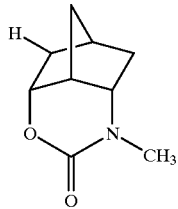

(d)

1.64 g of compound (c) are dissolved in 15 ml of dimethylformamide under argon and mixed with 565 mg of 50% sodium hydride whilst cooling with ice. Stirring is effected for 30 minutes, and then 1 ml of methyl iodide is added. The suspension is then stirred at room temperature for 18 hours. The reaction mixture is concentrated by evaporation on a rotary evaporator and the residue taken up with 50 ml of dichloromethane and 10 ml of saturated ammonium chloride solution. The organic phase is separated, washed with saturated aqueous NaCl solution (1×), dried over $MgSO_4$ and concentrated by evaporation on a rotary evaporator. After recrystallisation from diisopropylether, compound (d) is obtained as a white solid (1.3 g, 73% of theory). $^1$H-NMR (400 Hz, $DMSO_{d6}$), δ: 1.10 (1H); 1.20 (1H); 1.41 (2H); 1.92 (1H); 2.10 (1H); 2.20 (2H); 2.28 (1H); 2.37 (1H); 2.86 (1H); 3.68 (1H); 4.70 (1H).

b) Preparation of A3

Starting with 1.53 g of (d), and proceeding as in example A4, the title compound A3 is obtained as a colourless oil after purification by bulb tube distillation (0.5 g, 39% of theory).

B) Preparation of Metal Complexes

EXAMPLE B1

Under an inert gas (argon), 6.1 g (0.010 mmols) of $[RUCl_2(4\text{-cumene})]_2$, 2.8 mg (0.022 mmols) of compound A1 and 10 ml of absolute isopropanol are added in succession to a Schlenk flask. The mixture is stirred for 5 minutes at room temperature. The resulting solution is subsequently used further as a catalyst solution.

C) Hydrogenation

EXAMPLE C1

Preparation of 1-phenylethanol 120 mg (1.0 mmols) of acetophenone are added to the catalyst solution of example B1, and the solution is stirred for 5 minutes at room temperature. Subsequently, 2.4 ml of a 0.1 M NaOH solution in isopropanol are added, and the reaction is started, After 5 minutes, the reaction is interrupted, and the conversion and enantio-selectivity are determined. The conversion is 83%, and the enantiomers purity of the formed 1-phenylethanol is 88% ee.

Determination of conversion: Determination of conversion is carried out by gas chromatography (HP 5890A). Conditions: Capillary column DB 17 (50 m); starting temperature (60° C.), rate (3° C./minute), end temperature 140° C.

Determination of ee: Enantiomer separation is carried out by gas chromatography (Carlo Erba) with the capillary column Lipodex A (50 m×0.25 mm). Conditions: 90° C. isothermic, $H_2$ as carrier gas (150 kPa).

I claim:

1. Compounds of formula I

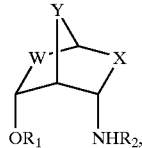

(I)

wherein

W signifies —$CH_2$—, X is —$CH_2$—, Y is —$CH_2$—, $R_1$ signifies hydrogen, $C_1$–$C_6$-alkyl, $C_2$–$C_6$-alkenyl, $C_3$–$C_8$-cycloalkyl, $C_3$–$C_8$-cycloalkenyl, $C_6$–$C_{10}$-aryl, or $C_7$–$C_{12}$-aralkyl, $R_2$ is hydrogen, $C_1$–$C_6$-alkyl, $C_3$–$C_8$-cycloalkyl, $C_6$–$C_{10}$-aryl, or $C_7$–$C_{12}$-aralkyl, $C_1$–$C_8$-carboxylic acyl, $C_1$–$C_6$-alkoxycarbonyl, $C_1$–$C_6$-alkylaminocarbonyl, di($C_1$–$C_6$-alkyl)aminocarbonyl, $(R_6)_2P(O)$—, or $R_6SO_2$—, and $R_6$ is $C_1$–$C_6$-alkyl, $C_1$–$C_6$-halogenalkyl; or cyclohexyl, phenyl or benzyl either unsubstituted or substituted by $C_1$–$C_4$-alkyl, $C_1$–$C_4$-halogenalkyl, or $C_1$–$C_4$-alkoxy; and the bicyclic ring system is unsubstituted or is substituted by $C_1$–$C_6$-alkoxy, cyclohexyl, $C_6$–$C_{10}$-aryl, $C_7$–$C_{12}$-aralkyl, $C_1$–$C_4$-alkyl-$C_6$–$C_{10}$-aryl, $C_1$–$C_4$-alkoxy-$C_6$–$C_{10}$-aryl, $C_1$–$C_4$-alkyl-$C_7$–$C_{12}$-aralkyl, $C_1$–$C_4$-alkoxy-$C_7$–$C_{12}$-aralkyl;

as well as the acid addition salts thereof.

2. Compounds according to claim 1, in which $R_2$ is $C_1$–$C_4$-alkyl, cyclopentyl, cyclohexyl, phenyl, benzyl, $C_1$–$C_4$-alkoxycarbonyl or the radical $R_6$—$SO_2$—, wherein $R_6$ is $C_1$–$C_4$-alkyl, $C_1$–$C_4$-fluoroalkyl, or phenyl either unsubstituted or substituted by one or two methyl or trifluoromethyl.

3. Compounds according to claim 1, whereby they correspond to formula Ia,

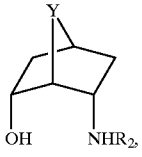

(Ia)

wherein Y signifies —$CH_2$— or —$CH_2CH_2$—, and $R_2$ is H, $C_1$–$C_4$-alkyl, or signifies the radical of formula $R_6$—$SO_2$—, and $R_6$ represents $C_1$–$C_4$-alkyl, phenyl or phenyl substituted by $C_1$–$C_4$-alkyl or by trifluoromethyl.

4. Compounds according to claim 1, in which $R_2$ is formyl, acetyl, propionyl, butyroyl or benzoyl.

5. Process for the preparation of compounds of formula I in the form of their racemates, mixtures of diastereoisomers or substantially pure diastereoisomers,

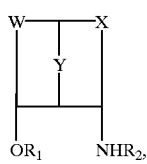
(I)

wherein

W signifies a direct bond or $C_1$–$C_4$-alkylene, X is a direct bond or $C_1$–$C_4$-alkylene, Y is $C_1$–$C_4$-alkylene, $R_1$ signifies hydrogen, $C_1$–$C_6$-alkyl, $C_2$–$C_6$-alkenyl, $C_3$–$C_8$-cycloalkyl, $C_3$–$C_8$-cycloalkenyl, $C_6$–$C_{10}$-aryl, or $C_7$–$C_{12}$-aralkyl, $R_2$ is hydrogen, $C_1$–$C_6$-alkyl, $C_3$–$C_8$-cycloalkyl, $C_6$–$C_{10}$-aryl, or $C_7$–$C_{12}$-aralkyl, $C_1$–$C_8$-carboxylic acyl, $C_1$–$C_6$-alkoxycarbonyl, $C_1$–$C_6$-alkylaminocarbonyl, di($C_1$–$C_6$-alkyl)aminocarbonyl, $(R_6)_2P(O)$—, or $R_6SO_2$—, $R_3$ signifies $C_1$–$C_6$-alkyl, cyclohexyl, phenyl or benzyl, $R_4$ and $R_5$, independently of one another, are $C_1$–$C_6$-alkyl, cyclohexyl, phenyl or benzyl, and $R_6$ is $C_1$–$C_6$-alkyl, $C_1$–$C_6$-halogenalkyl; or cyclohexyl, phenyl or benzyl either unsubstituted or substituted by $C_1$–$C_4$-alkyl, $C_1$–$C_4$-halogenalkyl, or $C_1$–$C_4$-alkoxy;

whereby aliphatic, saturated or ethylenically unsaturated and/or aromatic hydrocarbon rings are optionally condensed onto the rings of the bicyclic ring system, and the optionally condensed bicyclic ring system is unsubstituted or is substituted by $C_1$–$C_6$-alkyl, $C_1$–$C_6$-alkoxy, cyclohexyl, $C_6$–$C_{10}$-aryl, $C_7$–$C_{12}$-aralkyl, $C_1$–$C_4$-alkyl-$C_6$–$C_{10}$-aryl, $C_1$–$C_4$-alkoxy-$C_6C_{10}$-aryl, $C_1$–$C_4$-alkyl-$C_7$–$C_{12}$-aralkyl, $C_1$–$C_4$-alkoxy-$C_7$–$C_{12}$-aralkyl;

as well as the acid addition salts thereof, in which process a) a compound of formula II

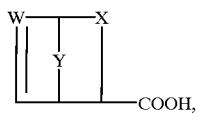
(II)

wherein W, X and Y are defined as indicated above, is reacted with a phosphoric acid ester azide in the presence of an alcohol R—OH, wherein R signifies $C_1$–$C_6$-alkyl, $C_5$–$C_8$-cycloalkyl, $C_5$–$C_8$-cycloalkyl-$C_1$–$C_4$-alkyl, benzyl, or benzyl substituted by $C_1$–$C_4$-alkyl, to form a compound of formula III,

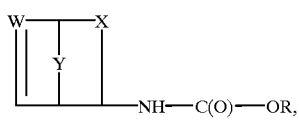
(III)

b) the compound of formula III is cyclised with bromine, iodine or an electrophilic brominating or iodising agent to form a compound of formula IV, wherein X' is Br or I,

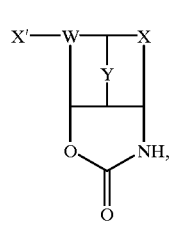
(IV)

c) in the compound of formula IV, the halogen is substituted by hydrogen to form a compound of formula V,

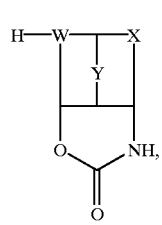
(V)

d) the compound of formula V is hydrolysed or reduced to the compound of formula VI,

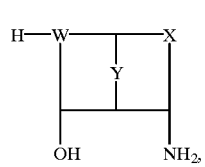
(VI)

e) or in the compound of formula V, the hydrogen atom of the NH group is substituted by the group $R'_2$ to form compounds of formula VII, wherein $R'_2$ signifies $C_1$–$C_6$-alkyl, $C_3$–$C_8$-cycloalkyl, $C_6$–$C_{10}$-aryl, or $C_7$–$C_{12}$-aralkyl, and then the compounds of formula VII are hydrolysed or reduced to compounds of formula VIII,

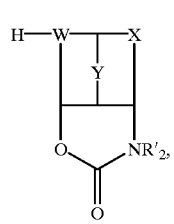
(VII)

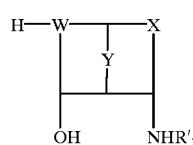
(VIII)

f) or the compounds of formula VI are reacted with $C_1$–$C_6$-alkoxycarbonates, $C_1$–$C_6$-alkylamino- or $C_1$–$C_6$-dialkylamino-carbonyl halides, $C_1$–$C_8$-carboxylic acid halides, $C_1$–$C_6$-alkoxy-carbonyl halides, $(R_6)_2P(O)$-halides or $R_6$—$SO_2$-esters or halides, to form compounds of formula IX, wherein $R''_2$ signifies $C_1$–$C_6$-alkoxycarbonyl, $C_1$–$C_8$-carboxylic acyl, $C_1$–$C_6$-alkylamino-, $C_1$–$C_6$- dialkylaminocarbonyl or the groups $(R_6)_2P(O)-$ and $R_6-SO_2-$,
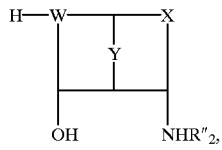
(IX)
g) and in compounds of formulae VI, VIII and IX, the OH group is etherified to compounds of formula X, $R_1$ signifies $C_1-C_6$-alkyl, $C_2-C_6$-alkenyl, $C_3-C_8$-cycloalkyl, $C_3-C_8$-cycloalkenyl, $C_6-C_{10}$-aryl, or $C_7-C_{12}$-aralkyl, and $R_2$ is defined as indicated for formula I,
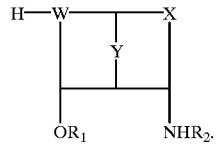
(X)
* * * * *